(12) United States Patent
Firstenberg et al.

(10) Patent No.: US 10,441,406 B2
(45) Date of Patent: *Oct. 15, 2019

(54) ANTI-MIGRATION MICROPATTERNED STENT COATING

(71) Applicant: Boston Scientific Scimed, Inc., Maple Grove, MN (US)

(72) Inventors: Laura Elizabeth Firstenberg, Worcester, MA (US); Claire M. McLeod, Stateline, NV (US); Shannon Taylor, Cary, NC (US); Andrea Lai, Auckland (NZ); Sandra Lam, Rancho Palos Verdes, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 440 days.

This patent is subject to a terminal disclaimer.

(21) Appl. No.: 13/857,998

(22) Filed: Apr. 6, 2013

(65) Prior Publication Data

US 2013/0268063 A1 Oct. 10, 2013

Related U.S. Application Data

(60) Provisional application No. 61/621,219, filed on Apr. 6, 2012.

(51) Int. Cl.
*A61F 2/04* (2013.01)
*A61F 2/06* (2013.01)
(Continued)

(52) U.S. Cl.
CPC ................. *A61F 2/06* (2013.01); *A61F 2/07* (2013.01); *A61F 2/90* (2013.01); *A61F 2/0077* (2013.01);
(Continued)

(58) Field of Classification Search
CPC ...... A61F 2/04; A61F 2/06; A61F 2/07; A61F 2/82; A61F 2002/044; A61F 2/0077; A61F 2250/0026; A61L 27/00
See application file for complete search history.

(56) References Cited

U.S. PATENT DOCUMENTS 6,042,605 A * 3/2000 Martin .................. A61F 2/07
 623/1.13
6,375,787 B1 * 4/2002 Lukic .................. A61F 2/07
 156/294

(Continued)

FOREIGN PATENT DOCUMENTS

JP 2006512099 A 4/2006
JP 2011509758 A 3/2011
(Continued)

OTHER PUBLICATIONS

PCT International Search Report, PCT International Application No. PCT/US2013/035531 (Filing Date: Apr. 6, 2013), dated Jul. 1, 2013, 3 pgs.

(Continued)

*Primary Examiner* — Dinah Baria
(74) *Attorney, Agent, or Firm* — Seager, Tufte & Wickhem, LLP

(57) ABSTRACT

An endoprosthesis has an expanded state and a contracted state, the endoprosthesis includes a stent having an inner surface defining a lumen and an outer surface; and a polymeric coating adhered to the outer surface of the stent. The polymeric coating includes a base and a plurality of protrusions extending outwardly from the base. When the endoprosthesis is expanded to the expanded state in a lumen defined by a vessel wall, the protrusions apply a force that creates an interlock between the vessel wall and the endoprosthesis.

21 Claims, 13 Drawing Sheets

(51) Int. Cl.
   *A61F 2/07*     (2013.01)
   *A61F 2/90*     (2013.01)
   *A61F 2/00*     (2006.01)
(52) U.S. Cl.
   CPC . *A61F 2002/044* (2013.01); *A61F 2230/0078* (2013.01); *A61F 2250/0026* (2013.01); *A61F 2250/0039* (2013.01)

(56) References Cited

U.S. PATENT DOCUMENTS

| | | | |
|---|---|---|---|
| 6,626,939 B1 * | 9/2003 | Burnside | A61F 2/07 623/1.38 |
| 6,872,439 B2 * | 3/2005 | Fearing | A44B 18/0003 24/442 |
| 7,744,914 B2 | 6/2010 | Li et al. | |
| 2002/0010489 A1 | 1/2002 | Grayzel et al. | |
| 2003/0004535 A1 | 1/2003 | Musbach et al. | |
| 2005/0203613 A1 | 9/2005 | Arney et al. | |
| 2005/0255230 A1 * | 11/2005 | Clerc et al. | 427/2.1 |
| 2005/0256564 A1 * | 11/2005 | Yang | A61F 2/86 623/1.42 |
| 2006/0069425 A1 | 3/2006 | Hillis et al. | |
| 2009/0062927 A1 | 3/2009 | Marten et al. | |
| 2009/0069904 A1 * | 3/2009 | Picha | 623/23.72 |
| 2009/0130372 A1 * | 5/2009 | Fukui | A44B 18/0053 428/92 |
| 2009/0187240 A1 | 7/2009 | Clerc et al. | |
| 2010/0076555 A1 | 3/2010 | Marten et al. | |
| 2011/0021965 A1 * | 1/2011 | Karp et al. | 602/54 |
| 2011/0172760 A1 | 7/2011 | Anderson | |
| 2012/0035715 A1 | 2/2012 | Robida et al. | |
| 2013/0218262 A1 | 8/2013 | Ishii et al. | |
| 2014/0276203 A1 | 9/2014 | Bertolino et al. | |
| 2014/0276407 A1 | 9/2014 | DeVries et al. | |
| 2014/0277395 A1 | 9/2014 | Firstenberg et al. | |
| 2014/0277443 A1 | 9/2014 | Fleury et al. | |

FOREIGN PATENT DOCUMENTS

| | | |
|---|---|---|
| JP | 2012065825 A | 4/2012 |
| WO | 0101887 A1 | 1/2001 |
| WO | 2014143750 A1 | 9/2014 |

OTHER PUBLICATIONS

PCT Written Opinion of the International Searching Authority, PCT International Application No. PCT/US2013/035531 (Filing Date: Apr. 6, 2013), dated Jul. 1, 2013, 5 pgs.

Axisa et al., "Low cost, biocompatible elastic and conformable electronic technologies using mid in stretchable polymer," Proceedings of the 29th Annual International Conference of the IEEE Eng. Med. Biol. Soc., Cite Internationale, Lyon, France, Aug. 23-26, 2007, 2007:6592-6595.

Conigliaro et al., "Polyflex stents for malignant oesophageal and oesophagogastric stricture: a prospective, multicentric study," European Journal of Gastroenterology & Hepatology, Mar. 2007, 19(3): 195-203.

Conio et al., "A Randomized Prospective Comparison of Self-Expandable Plastic Stents and Partially Covered Self-Expandable Metal Stents in the Palliation of Malignant Esophageal Dysphagia," Am. J. Gastroenterol., Dec. 2007, 102(12): 2667-2677.

Desai et al., "Plastic Masters-rigid templates for soft lithography." Lab on a Chip, Jun. 7, 2009, 9(11): 1631-1637. Available online Mar. 5, 2009.

Dodou et al., "Mucoadhesive micropatterns for enhanced grip," Proceedings of the 29th Annual International Conference of the IEEE Eng. Med. Biol. Soc., Cite Internationale, Lyon, France, Aug. 23-26, 2007, 2007:1457-1462.

Jeong et al., "Nanohairs and nanotubes: Efficient structural elements for gecko-inspired artificial dry adhesives," NanoToday, Aug. 2009, 4(4): 335-346.

Kroetch, "NanoFab's PDMS Microfluidic Device Fabrication Manual," Sep. 2004, University of Alberta, NanoFab—A Micromachining and Nanofabrication Facility, Edmonton, AB, Canada, 8 pgs.

Kwon et al., "Friction enhancement via micro-patterned wet elastomer adhesives on small intestinal surfaces," Biomedical Materials, Dec. 2006, 1(4): 216-220. Available online Oct. 20, 2006.

Lötters et al., "The mechanical properties of the rubber elastic polymer polydimethylsiloxane for sensor applications," Journal of Micromech. Microengineering, Sep. 1997, 7(3): 145-147.

Mahdavi et al., "A biodegradable and biocompatible gecko-inspired tissue adhesive," Proceedings of the National Academy of Sciences U S A, Feb. 19, 2008, 105(7): 2307-2312. Available online Feb. 19, 2008.

Majidi, "Enhanced Friction and Adhesion with Biologically Inspired Fiber Arrays," Technical Report EECS-2007-55, University of California at Berkeley, Electrical Engineering and Computer Sciences, May 15, 2007 (available online at http://www.eecs.berkeley.edu/Pubs/TechRpts/2007/EECS-2007-55.pdf (last accessed Jul. 2, 2013)).

Schembre, "Advances in esophageal stenting: the evolution of fully covered stents for malignant and benign disease," Advanced Therapy, Jul. 2010, 27(7): 413-425. Available online Jun. 28, 2010.

Sharma et al., "Role of esophageal stents in benign and malignant diseases," American Journal of Gastroenterology, Feb. 2010, 105(2): 258-273. Available online Dec. 22, 2009.

Shim, "Esophageal stenting in unusual situations," Endoscopy, Aug. 2003, 35(8): S14-S18.

Tooley et al., "Thermal fracture of oxidized polydimethylsiloxane during soft lithography of nanopost arrays," Journal of Micromechanics and Microengineering, May 2011, 21(5): 054013-1 to 054013-9.

Van Boeckel et al., "A new partially covered metal stent for palliation of malignant dysphagia: a prospective follow-up study," Gastrointestinal Endoscopy, Dec. 2010, 72(6): 1269-1273. Available online Oct. 16, 2010.

Ara'Nzazu del Campo, et al., "Contact Shape Controls Adhesion of Bioinspired Fibrillar Surfaces," Langmuir, vol. 23, No. 20, 2007, pgs. 10235-10243.

* cited by examiner

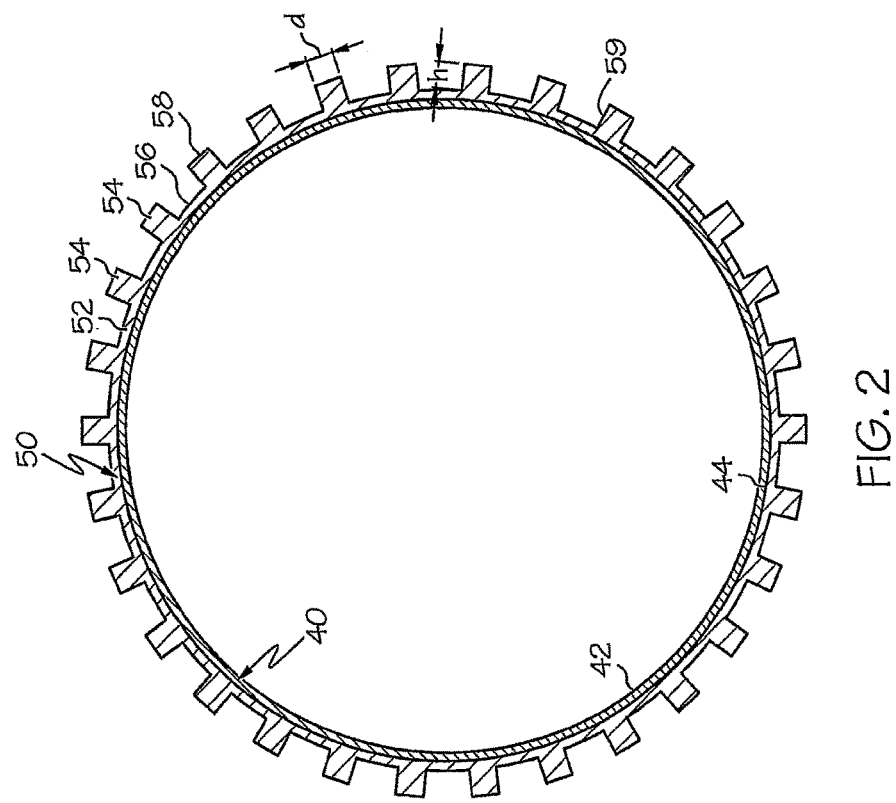
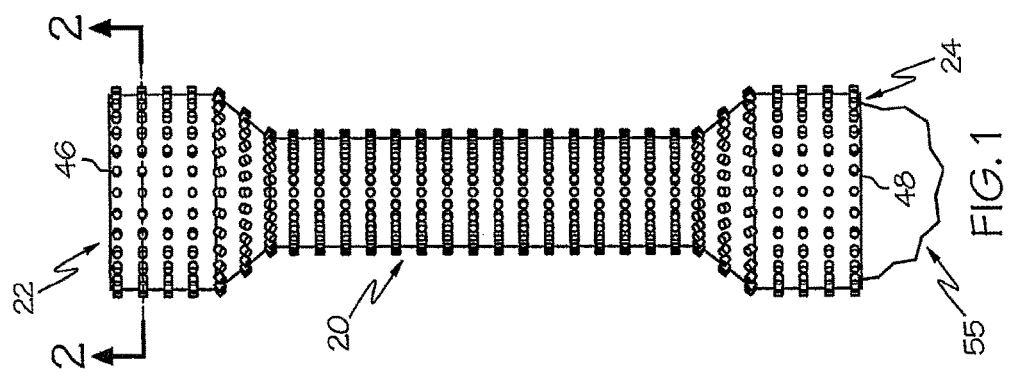

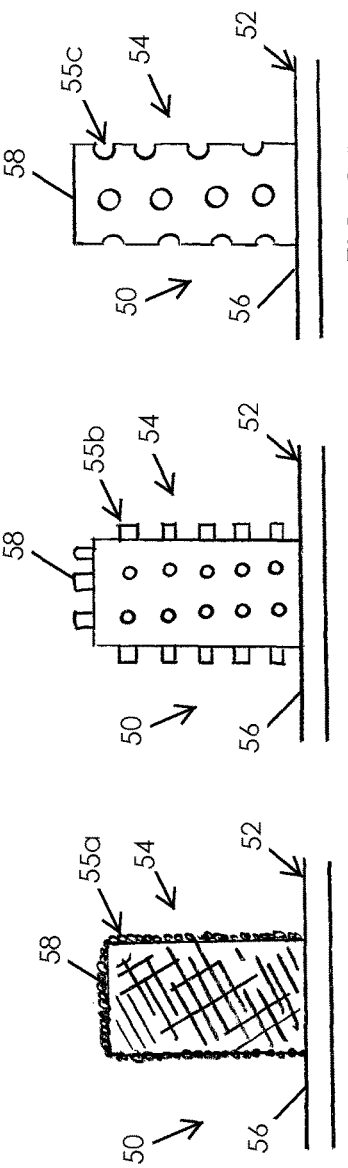
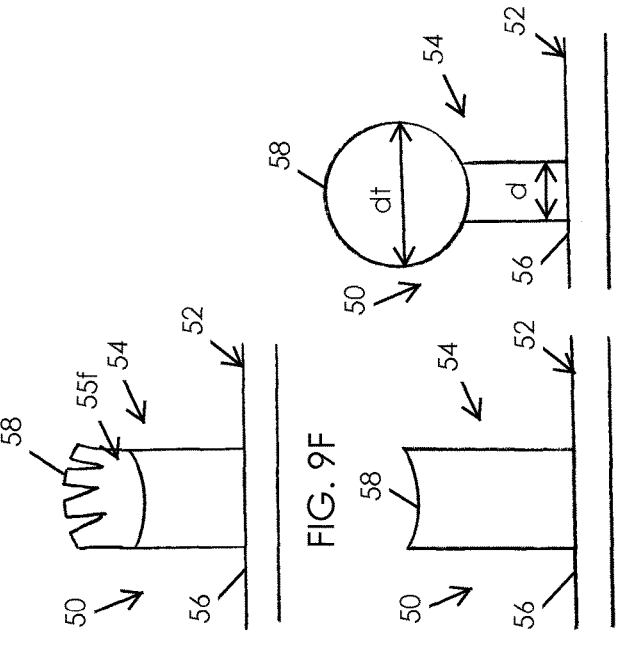
FIG. 9A  FIG. 9D  FIG. 9G
FIG. 9B  FIG. 9E  FIG. 9H
FIG. 9C  FIG. 9F  FIG. 9I
FIG. 9J

ANTI-MIGRATION MICROPATTERNED STENT COATING

CROSS REFERENCE TO RELATED APPLICATIONS

This patent application is a claims priority to and the benefit of U.S. Provisional Patent Application No. 61/621,219, entitled ANTI-MIGRATION MICROPATTERNED STENT COATING filed Apr. 6, 2012, which is herein incorporated by reference in its entirety.

BACKGROUND OF THE INVENTION

A stent is a medical device introduced into a body lumen and is well known in the art. A stent may be delivered in an unexpanded state to a desired location in a bodily lumen and then expanded by an internal radial force. Stents, grafts, stent-grafts, vena cava filters, expandable frameworks, and similar implantable medical devices, collectively referred to hereinafter as stents, have included radially expandable endoprostheses, which have been used as intravascular implants capable of being implanted transluminally.

Esophageal stents have been used to treat patients suffering from a range of malignant and non-malignant diseases. Most commonly, esophageal stents have been associated with the treatment of esophageal cancers. Esophageal stents have also been used to reduce symptoms resulting from non-esophageal tumors that grow to obstruct the esophagus and to treat benign esophageal disorders, including but not limited to refractory strictures, fistulas and perforations. In each of these cases, esophageal stents may provide mechanical support to the esophageal wall and may maintain luminal patency. Because of the structure of the esophagus and conditions such as peristalsis, esophageal stents have been prone to stent migration.

One way to reduce the risk of stent migration has been to expose bare metal portions of the stent to esophageal tissue. The open, braided structure of the stent may provide a scaffold that promotes tissue ingrowth into the stent. This tissue ingrowth may aid anchoring the stent in place and may reduce the risk of migration. In some cases, however, tissue ingrowth has been known to lead to reocclusion of the esophagus. In addition, esophageal stents anchored by tissue ingrowth cannot be moved or removed without an invasive procedure. To reduce tissue ingrowth, stents have been covered with a coating (e.g., made of a polymer, etc.) to create a physical barrier between the lumen and the esophageal wall. However, in some circumstance, such stents can have an unacceptable occurrence of migration, as compared to bare metal counterparts.

Another way to reduce the risk of stent migration has been to use a flared stent in the esophagus. However, stents having flares can have an unacceptable occurrence of migration.

Improved stents with, for example, improved resistance to migration, improved stent adhesion to the esophageal wall, and/or improved removability are desired. Previous tracheal stents, such as those discussed in US Patent Publication Nos. 2006/0069425 and 2009/0062927, which are incorporated by reference herein in their entireties, have incorporated bumps or other surface features incorporated into the stent itself. Another tracheal stent described in co-owned US Patent Publication No. 2012/0035715, which is incorporated by reference herein in its entirety, provides a plurality of surface protrusions on the outer surface of the stent.

Without limiting the scope of the present disclosure, a brief summary of some of the claimed embodiments is set forth below. Additional details of the summarized embodiments of the present disclosure and/or additional embodiments of the present disclosure may be found in the Detailed Description of the Invention below. A brief abstract of the technical disclosure in the specification is also provided. The abstract is not intended to be used for interpreting the scope of the claims.

BRIEF SUMMARY OF THE INVENTION

The present disclosure provides an endoprosthesis where a preferably polymeric coating has a number of surface features such as protrusions that are arranged in a micropattern. As used herein, a micropattern may include a regular or irregular array of micro-scale features (e.g., protrusions such as micropillars). Generally, micro-scale feature means a feature having a dimension (e.g., length, width, or height) in a range of from about 1 micrometer to about 999 micrometers. Herein, unless the context indicates otherwise, micro-scale features are referred to as micropillars (e.g., extending from a base).

In at least one embodiment, an endoprosthesis, having an expanded state and a contracted state, includes a stent with a polymeric coating adhered to an outer surface of the stent. The stent has an inner surface defining a lumen. In at least one embodiment, the stent is a flared stent. The polymeric coating includes a base and a plurality of protrusions (e.g., micropillars, etc.) extending outwardly from the base. In at least one embodiment, the protrusions are arranged in a micropattern. When the endoprosthesis is expanded to the expanded state in a lumen defined by a vessel wall, the micropillars apply a force that creates an interlock between the vessel wall and the endoprosthesis.

Although not wishing to be bound by theory, tissue may engage a micropatterned coating as a result of one or more mechanisms. For example, tissue may interlock with a micropatterned coating having one or more micropillars by growing around and/or between the one or more micropillars. In one or more embodiments, a chemical bond mechanism may be formed between a tissue in contact with a micropatterned coating that may include, for example, a mucoadhesive gel. In one or more embodiments, engagement of tissue with a micropattern having an appropriate geometry may be by proximity attraction by van der Waals bonding.

The micropattern is specifically designed for a particular tissue in order to effectively interlock the stent with the tissue. In at least one embodiment, the micropattern is present along at least a portion of the endoprosthesis. In at least one embodiment, the protrusions of the micropattern can be uniform or the micropattern can be formed of protrusions having a first configuration and protrusions having at least a second configuration.

The protrusions may be micropillars and may be selected from a group including cylinders, rectangular prisms, and similar structures. In at least one embodiment, the protrusions of the micropattern are cylindrical micropillars, each cylindrical micropillar having a diameter and a height, wherein the diameter of each cylindrical micropillar is equal to its height. In at least one embodiment, the cylindrical micropillar has a lateral surface, wherein the lateral surface of the cylindrical micropillar is separated from the lateral surfaces of an adjacent micropillar by a distance greater than the diameter of the cylindrical micropillar. In at least one embodiment, the micropattern is a grid pattern.

In at least one embodiment, each protrusion of the micropattern has a first dimension and a second dimension, wherein the first dimension is between about 1 µm and 999 µm (e.g., between about 1 µm and 100 µm), wherein the second dimension is between about 1 µm and 999 µm (e.g., between about 1 µm and 100 µm), and wherein each protrusion is spaced apart from an adjacent protrusion by a distance, wherein a ratio between the distance and the first dimension is between about 2.1 and 2.4. In at least one embodiment, each protrusion has a ratio between the first dimension and the second dimension that is between about 1 and 1.3.

In at least one embodiment, the endoprosthesis is retrievable by, for example, a retrieval loop at a distal end of the stent.

Several methods of manufacturing an embodiment of the endoprosthesis are provided. One method of manufacturing includes forming a polymeric coating, wherein the polymeric coating includes a base and a plurality of protrusions extending outwardly from the base in a micropattern; providing a stent having an inner surface defining a lumen and an outer surface; and adhering the base of the polymeric coating to the outer surface of the stent. The polymeric coating can be formed using a mold having an inverse of the micropattern and injecting a polymeric material into the mold and, in some cases applying temperature or pressure to the mold, before the polymeric material cures; using soft lithography techniques, or by etching the polymeric coating from a layer of the polymeric material. In at least one embodiment, an adhesive layer is applied to at least one of a surface of the base and the outer surface of the stent. In at least one embodiment, the polymeric coating is formed as a tubular structure. In one or more embodiments, the polymeric coating is formed in a strip, which is wrapped (e.g., helically wrapped, circumferentially wrapped, randomly wrapped, etc.) about the outer surface of the stent.

BRIEF DESCRIPTION OF THE SEVERAL VIEWS OF THE DRAWING(S)

FIG. 1 shows a plan view of the endoprosthesis of the present disclosure.

FIG. 2 shows a cross-section of the endoprosthesis shown in FIG. 1.

FIGS. 9A-9J show plan views of embodiments of the polymeric coating shown in FIG. 3.

DETAILED DESCRIPTION OF THE INVENTION

Figure 3:
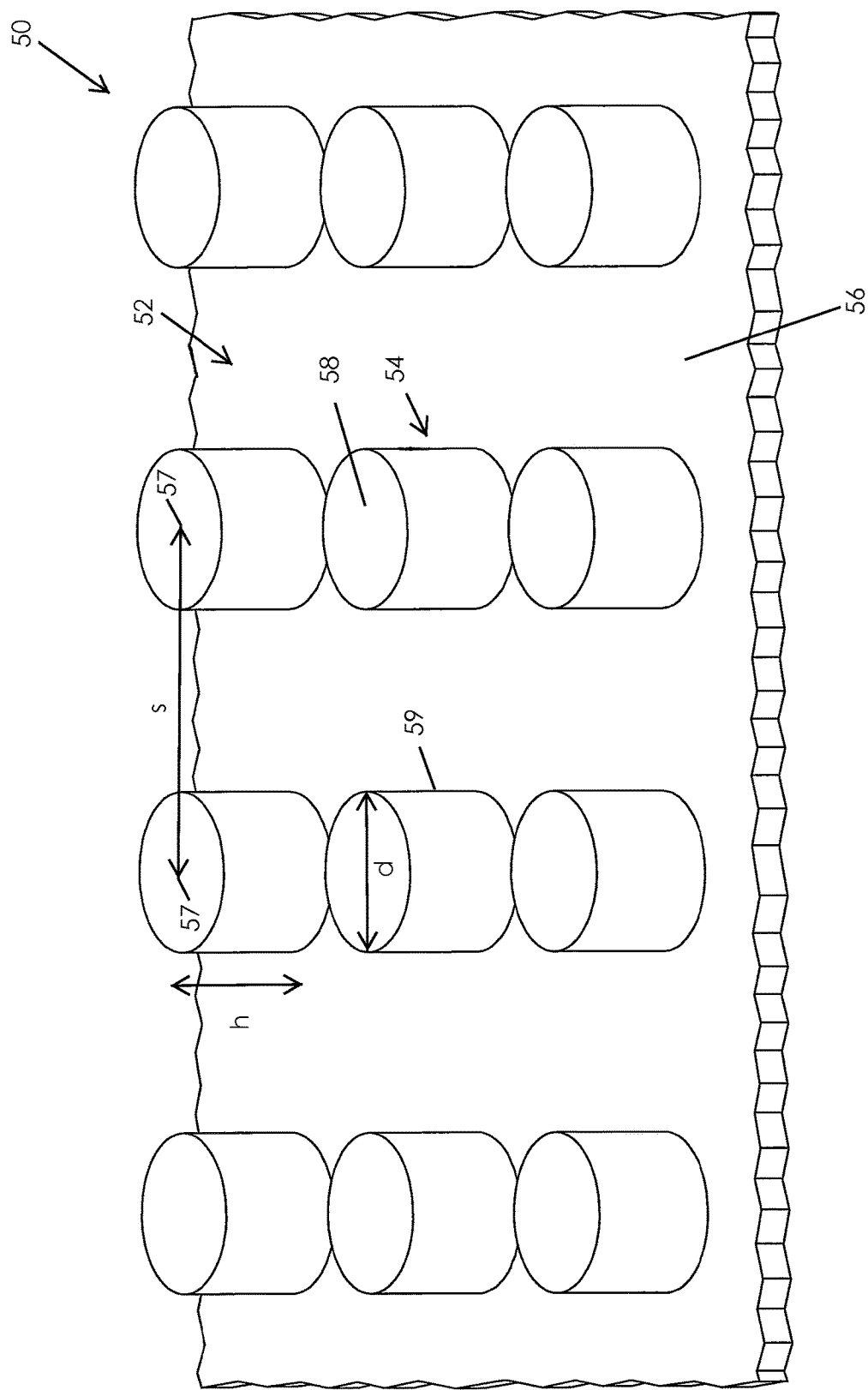
FIG. 3 is an enlarged view of the polymeric coating of the endoprosthesis shown in FIG. 1.
Figure 6:
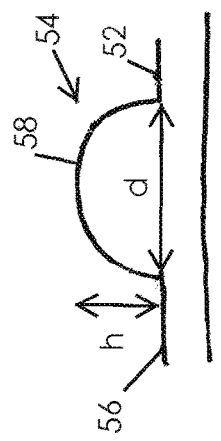
FIGS. 5-7 show cross-sections of portions of embodiments of the polymeric coating.

While the subject matter of the present disclosure may be embodied in many different forms, there are described in detail herein specific preferred embodiments of the present disclosure. This description is an exemplification of the principles of the present disclosure and is not intended to limit the present disclosure to the particular embodiments illustrated.

For the purposes of this disclosure, like reference numerals in the figures shall refer to like features unless otherwise indicated.

The present disclosure relates to micropatterned polymeric coatings for use on medical devices. In some embodiments, the micropatterned polymeric coatings are utilized with implantable medical devices, such as stents, to reduce or prevent stent migration, particularly for stents used in the gastroesophageal system, including, but not limited to, esophageal, biliary, and colonic stents. The stents described in this application may be used in the trachea, the cardiovascular system, and elsewhere in the body (e.g., any body lumen).

FIGS. 1 and 2 show an esophageal endoprosthesis 20 of the present disclosure with a proximal end 22 and a distal end 24. The endoprosthesis 20 includes an expandable stent 40 and a polymeric coating 50. Expandable stent 40 can be self-expanding, balloon expandable, or hybrid expandable. Embodiments of the expandable stent 40 contemplate stents having a constant diameter, tapers, flares and/or other changes in diameter in the body and/or at an end. The expandable stent 40 has an inner surface 42, an outer surface 44, a first end 46 and a second end 48, and the polymeric coating 50 is disposed about at least a portion of the outer surface 44. In at least one embodiment, the polymeric coating 50 substantially covers the entire outer surface 44 of the expandable stent 40. In other embodiments, the polymeric coating 50 covers a portion of the outer surface 44 of the expandable stent 40. As shown in FIG. 2, the polymeric coating 50 can be directly connected to the outer surface 44 of the expandable stent 40. In one or more embodiments, the polymeric coating 50 can be connected to the outer surface 44 of the expandable stent 40 using an adhesive or other means of attaching the coating to the device. In at least one embodiment, the polymeric coating at least partially covers the inner surface 42 also. In at least one embodiment, partial coverage can include partial coverage of the perimeter and/or the length.

In at least one embodiment, shown in FIGS. 2 and 3, the polymeric coating 50 includes a base 52 and a plurality of protrusions, such as micropillars 54, extending outwardly from the base 52. In at least one embodiment, the micropillars are seamlessly incorporated into the base of the coating. In at least one embodiment, the base 52 is coterminous with the expandable stent 40. What is meant by "coterminous" is that the base 52 of the polymer coating 50 and the expandable stent 40 have the same boundaries, cover the same area, and are the same in extent. In other words, the expandable stent 40 and the base 52 each have first and second ends, and the expandable stent 40 and the base 52 extend between their first and second ends. The first end of the expandable stent 40 is the same as first end of the base 52, and the second end of the expandable stent 40 is the same as the second end of the base 52. Since the expandable stent 40 and the base 52 extend between their first and second ends, the expandable stent 40 and the base 52 have the same boundaries, cover the same area, and are the same in extent. Thus, the base 52 and the expandable stent 40 are coterminous. The expandable stent 40 and the base 52 therefore are coterminous in at least one embodiment. Also, base 52 is tubular in at least one embodiment.

Figure 7:
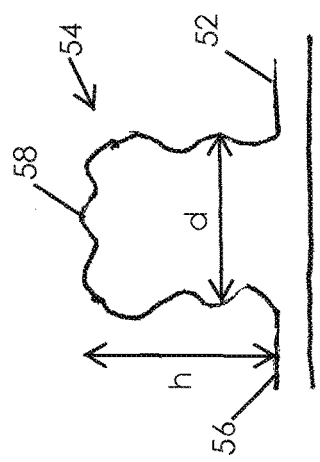
Figure 4:
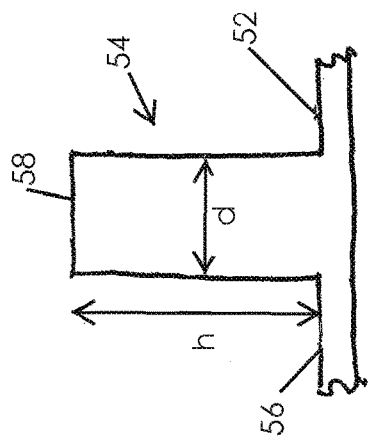
FIG. 4 shows a cross-section of a portion of the polymeric coating shown in FIG. 3.
Figure 5:
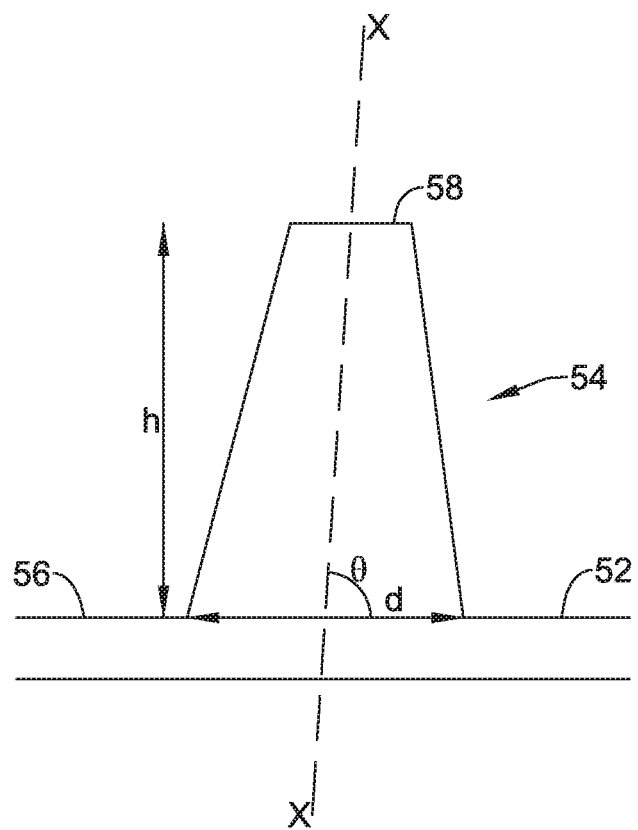
Figure 8A:
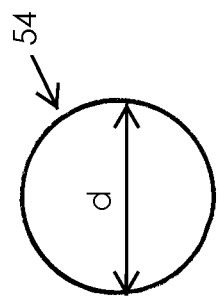
FIGS. 8A-8J show cross-sections of the micropillars of the polymeric coating shown in FIGS. 3-6.
Figure 8B:
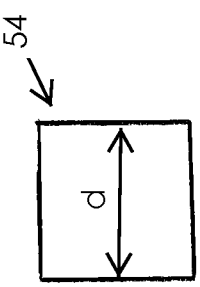
Figure 8C:
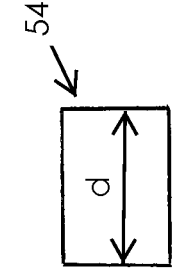
Figure 8D:
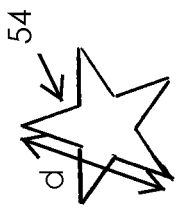
Figure 8E:
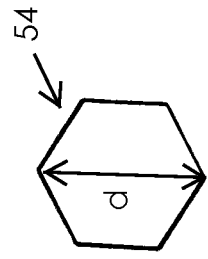
Figure 8F:
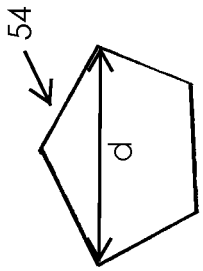
Figure 8G:
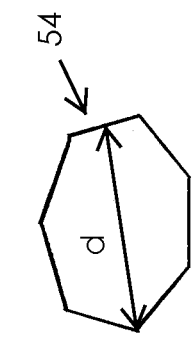
Figure 8H:
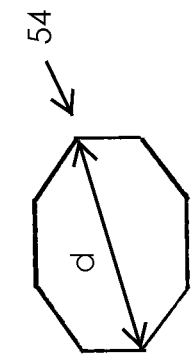
Figure 8I:
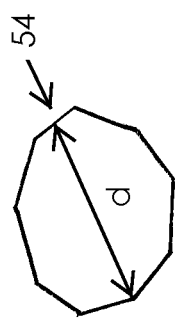
Figure 8J:
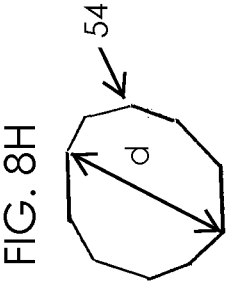

In some embodiments as shown in FIGS. 3-7, the micropillars are cylinders (FIG. 3), prisms with a rectangular or polygonal base (FIG. 4), pyramids (FIG. 5), bumps (FIG. 6), or has a non-traditional shape with a plurality of bumps and ridges on multiple surfaces that do not define a cross-section that is circular, square, polygonal, etc. (FIG. 7). Each micropillar can have a circular cross-section (FIG. 8A), square cross-section (FIG. 8B), rectangular cross-section (FIG. 8C), star-shaped cross-section (FIG. 8D), hexagonal cross-section (FIG. 8E), pentagonal cross-section (FIG. 8F), heptagonal (FIG. 8G), octagonal cross-section (FIG. 8H), nonagonal cross-section (FIG. 8I), decagonal cross-section (FIG. 8J), other polygonal cross-sections, or non-traditional shaped cross-sections. Each cross-section has a first dimension h that is the greatest distance between the outer surface of the base and the end of the pillar and a second dimension d that is the greatest distance between two opposite sides (e.g., of the pillar). For example, for the circular cross-section the second dimension d is the diameter, for the square d is between two sides, for the rectangle, the major dimension is between the two shorter sides, for the star, the major dimension is between two points, for the hexagon the major dimension is between two opposite points. In some embodiments, the second dimension d is between midpoints of two opposite sides. In at least one embodiment, a cross section of the micropillar taken in the radial direction has at least four sides. Embodiments of the present disclosure contemplate polygonal cross-sections having all sides of equal length, combinations of sides of equal length and unequal length, or all sides of unequal length. Embodiments of the present disclosure contemplate multiple pillars of multiple cross-sectional shapes including traditional shapes (e.g. circles, squares, rectangles, hexagons, polygons, etc.) and non-traditional shapes having a perimeter where at least a portion of the perimeter is curvilinear. In at least one embodiment, the micropillars are solid structures, but in other embodiments they can be hollow structures. In at least one embodiment, each micropillar has a constant cross-section, but in other embodiments the micropillars have variable cross-sections. In at least one embodiment, a micropillar extends perpendicularly from a base (e.g., FIG. 4). In at least one embodiment, a micropillar extends from a base in a non-perpendicular angle (e.g., FIG. 5) wherein geometric center 57 (see FIG. 3) of the top surface 58 of the micropillar is offset laterally from the geometric center of the area of the base covered by the micropillar (e.g., FIG. 5). In FIG. 5, a longitudinal axis X-X of the micropillar 54 extending through the geometric centers of the cross-sections forms an angle θ that is less than 90 degrees with base 52. In at least one embodiment, the plurality of micropillars 54 can be arranged in one or more particular micropatterns. Although not wishing to be bound by theory, the micropattern may affect the strength of the frictional engagement or interlock between the endoprosthesis and the vessel wall. Likewise, the micropattern is dependent upon the desired frictional engagement or interlock between the micropillars of the endoprosthesis and the tissue. For this reason, in at least one embodiment, a particular microstructure can be selected that has a micropattern geometry and dimensions suitable for a particular application (e.g., implantation site, biological tissue, desired tissue engagement properties, etc.).

It should be noted that the surface features of micropillars or holes described herein (e.g., bumps of FIG. 6, bumps and ridges of FIG. 7, etc.) may have one or more micro-scale or nano-scale (e.g., from about 1 nanometer to about 999 nanometers) dimensions.

In at least one embodiment, the micropillars in the micropattern all have the same shape, and in other embodiments, the micropillars vary in shape along the polymeric coating. Thus, in at least one embodiment, the micropattern can include portions where the micropillars have a first configuration and portions where the micropillars have a second configuration. Moreover, embodiments include the polymeric coating having only one micropattern or the polymeric coating having multiple micropatterns. Thus, the polymeric coating can be tailored to specific structural characteristics of the body lumen (e.g., a vessel, etc.) and a desired frictional engagement or interlock can be achieved, while using a single stent.

In at least one embodiment, the dimension d is between 1 μm and 100 μm. In at least one embodiment, the dimension d is between about 14 μm and 18 μm. In at least one embodiment, the dimension d is at least equal to the dimension h. In at least one embodiment, a ratio of h to d is between about 1 and 1.3. In at least one embodiment, two adjacent micropillars are spaced apart by a distance s (shown in FIG. 3). In at least one embodiment, the ratio of the spacing s to the dimension d is between about 2.1 and 2.4.

In some embodiments, the ends of the protrusions, such as micropillars 54, that are furthest away from the outer surface of the base can be shaped to improve tissue attachment. In one or more embodiments, the ends can be tapered, pointed, rounded, concave, convex, jagged, or frayed. The ends of each protrusion (micropillar 54) can include a plurality of pillars on an even smaller scale than micropillars 54.

In at least one embodiment, the protrusions such as micropillars 54 can also include features such as smooth surfaces, rough surfaces 55a (FIG. 9A), a plurality of bumps 55b extending outwardly from a surface of the micropillar (FIG. 9B), a plurality of indentations 55c extending inwardly from a surface of the micropillar (FIG. 9C), a plurality of ridges 55d on a surface of the micropillar (FIG. 9D), a tip 55e at or near the end of the protrusion that either softer or more rigid than the remainder of the protrusion (FIG. 9E), a frayed tip 55f (FIG. 9F), a convex (e.g., rounded) tip (FIG. 9G), a flared (e.g., flat top) tip (FIG. 9H), a concave (e.g., rounded) tip (FIG. 9I), a tip having a first dimension dt that is greater than a dimension d of the micropillar column extending between the base 52 and the tip (FIG. 9J), and other features that may impart desirable gripping, stiffness, or flexibility characteristics for the endoprosthesis, and any combination of features thereof. In at least one embodiment, the tip 55e can include a different material than the remainder of the protrusion.

FIG. 3 shows an enlarged view of the polymeric coating 50. In at least one embodiment, the micropillars are cylinders that each have a diameter d and a height, h measured from an outer surface of the base 56 to a top surface of the cylinder 58. In at least one embodiment, the diameter d is between 1 μm and 150 μm (e.g., between 1 μm and 100 μm, between 1 μm and 50 μm, between 1 μm and 20 μm, etc.). In at least one embodiment, the diameter d is between about 14 μm and 18 μm. In at least one embodiment, the diameter d of the micropillar is at least equal to its height h. In at least one embodiment, a ratio of height h of the micropillar 54 to diameter d of the micropillar is between about 1 and 1.3. In at least one embodiment, the micropillars each have a lateral surface 59. In at least one embodiment, two adjacent micropillars are spaced apart. The micropillars should be spaced apart enough so that the tissue of the bodily vessel can fill the negative space (e.g., void space) between the pillars. If the spacing is too small, the tissue may not be able to actually interlock. In at least one embodiment, the spacing between the micropillars is dependent upon (e.g., may be selected based upon) the particular type of tissue of the bodily vessel. In at least one embodiment, the spacing s measured between the centers 57 of one micropillar and an adjacent micropillar is greater than the diameter d of the one micropillar. In at least one embodiment, the ratio of the spacing s to the diameter d is between about 2.1 and 2.4.

Figure 10A:
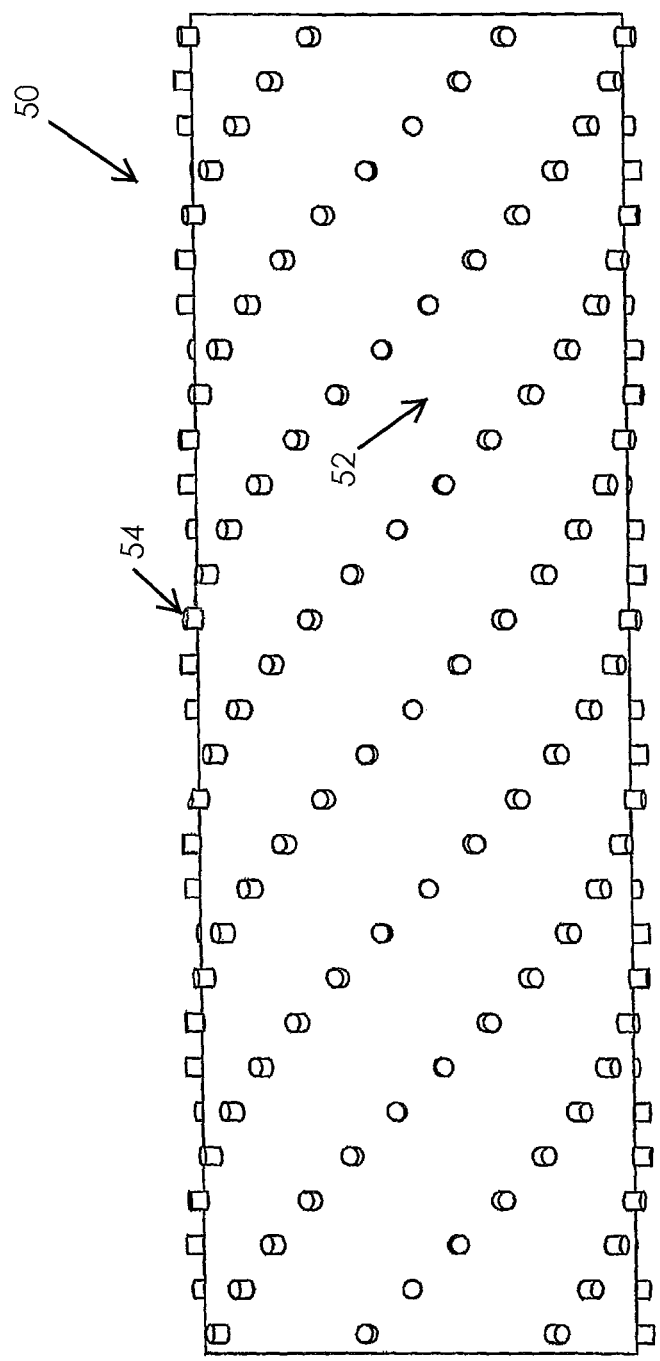
FIG. 10A shows an embodiment of the polymeric coating of the present disclosure.
Figure 10B:
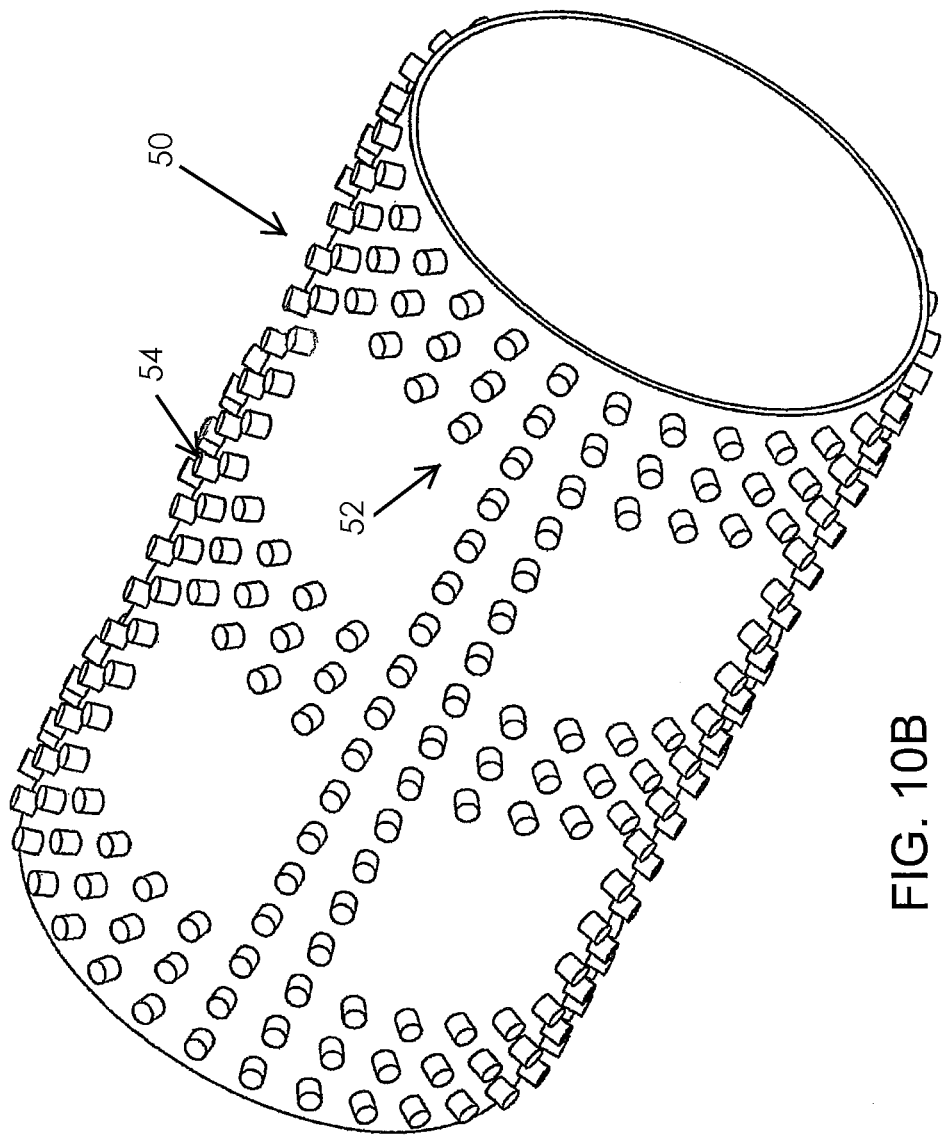
FIG. 10B shows an embodiment of the polymeric coating of the present disclosure.
Figure 10E:
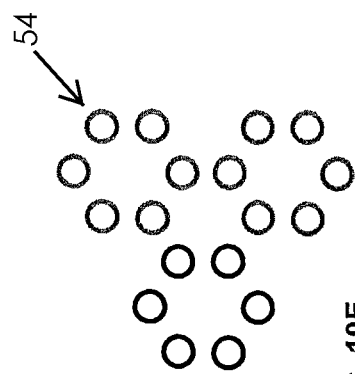
FIGS. 10C-10E show embodiments of arrays of micropillars forming a micropattern.
Figure 10D:
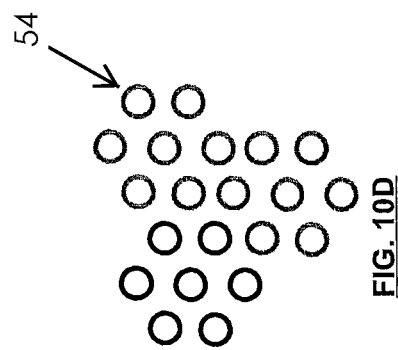
Figure 10C:
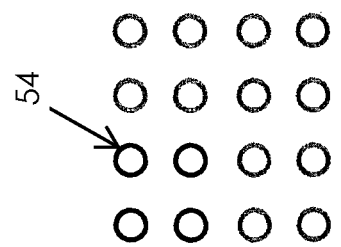

In at least one embodiment, the micropillars are spaced apart equidistantly in the micropattern. In at least one embodiment, the micropattern of micropillars is a rectangular array (e.g., FIG. 3, FIG. 10C). In at least one embodiment, the micropattern is a grid pattern (e.g., a square array as in FIGS. 10C, 11). In at least one embodiment, the micropattern is a regular n-polygonal array (e.g., hexagonal array in FIGS. 10D, 10E), wherein a micropillar may be present in the center of the polygon (e.g., FIG. 10C, FIG. 10D, etc.) or may not be present in the center of the polygon (e.g., FIG. 10E). In other words, in the micropattern, the micropillars are arranged in rows and columns in the micropattern, wherein the rows and columns may or may not be perpendicular. For example, the micropattern of FIG. 10C includes rows and columns that are perpendicular, whereas the micropattern of FIGS. 10D and 10E includes rows and columns that are not perpendicular. In one or more embodiments, each micropillar has a longitudinal axis and the micropillars are axially aligned in at least one of the axial direction (e.g., arranged in a row parallel to a longitudinal axis of a stent) and the circumferential direction of the endoprosthesis (e.g., arranged in a row extending circumferentially around a longitudinal axis of a stent). In at least one embodiment, the micropattern of micropillars includes any or all of the features described in this paragraph. In some embodiments, like the embodiments shown in 10A and 10B, the micropattern may cover only a portion of the base 52 rather than the entire base 52. The micropattern of micropillars may be helically disposed on the base 52, as shown in FIG. 10A. In one or more embodiments, as shown in FIG. 10B, a first micropattern may be disposed longitudinally along the base 52 and a second micropattern is disposed circumferentially about the base so that the micropattern forms a "window pane"-like configuration. As depicted in FIG. 10B, the micropillars arranged in a row (e.g., parallel to a longitudinal axis of a stent) may be continuous rows or discontinuous rows (e.g., aligned row segments separated by a gap having a dimension greater than s), wherein the length of the discontinuity may have any length (e.g., 2 or more times the dimension s). For example, the embodiment depicted in FIG. 10B shows discontinuous rows (and circumferentially oriented columns) extending across the window panes wherein the length of the discontinuity is five times the dimension s (see FIG. 3) whereas the embodiment depicted in FIG. 10E shows discontinuous rows (and non-perpendicularly oriented columns) wherein the length of the discontinuity is two times the dimension s (see FIG. 3). In terms of the dimension s shown in FIG. 3, a row and/or column discontinuity may have any length (e.g., at least 2 times s, at least 5 times s, at least 10 times s, at least 50 times s, at least 100 times s, at least 500 times s, at least 1000 times s, etc.).

Regarding the material used for the polymeric coating 50, it is important that the material be flexible enough to create an effective interlock with the tissue and be able to withstand the processing for creating the polymer coating 50. Examples of acceptable materials include, but are not limited to, flexible silicones, hydrogels, mucoadhesive substrate, pressure-sensitive adhesives, and other suitable elastomers, such as synthetic rubbers. Other acceptable materials include any flexible, biocompatible, and non-biodegradable polymer. In at least one embodiment, the polymeric coating 50 (e.g., having micropillars 54) may include proteins capable of engaging the tissue wall in a biochemical manner. In at least one embodiment, the polymeric coating 50 may include at least one therapeutic agent. In other embodiments, an additional coating may be applied to the polymeric coating 50 that includes a therapeutic agent. A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof.

In a preferred embodiment, the micropillars 54 and the base 56 are formed from the same material. In one or more embodiments, the micropillars 54 are formed from one material and the base 56 is formed from a different material. In one or more embodiments, the micropillars 54 are formed with layers of material, and these layers can be the same material or can be different materials depending on the characteristics required for the desired frictional engagement of the endoprosthesis with the vessel wall.

Because the endoprosthesis 20 has improved frictional engagement with the tissue wall when inserted into a lumen of the patient, removal of the stent may be more difficult with some traditional removal techniques. In at least one embodiment, shown in FIG. 1, the endoprosthesis 20 is provided with a suture or removal loop 55 on one end of the stent. In at least one embodiment, the removal loop 55 is provided on a distal end of the stent. It should be noted that references herein to the term "distal" are to a direction away from an operator of the devices of the present disclosure, while references to the term "proximal" are to a direction toward the operator of the devices of the present disclosure. While sutures or removal loops are well known in the art for removing endoprosthesis, typically sutures or removal loops are provided on the proximal end of the stent, in other words the closest end to the practitioner. Here, the suture or removal loop is applied to the opposite end of the endoprosthesis. In at least one embodiment, the practitioner grabs the loop from inside the endoprosthesis, and by applying an axial force to the loop, the distal end of the endoprosthesis is pulled through the lumen of the endoprosthesis itself. Thus, the micropillars are peeled away from the vessel wall while the stent is flipped inside out to remove the endoprosthesis. In other embodiments, the practitioner may grab the loop from outside the endoprosthesis or at an end of the endoprosthesis.

To manufacture the endoprosthesis 20, several methods can be employed. The polymeric coating 50 can be molded separately from the stent and then adhered to the stent with an adhesive layer 60 between the outer surface of the endoprosthesis and the base of the polymeric coating. Polymeric material can be injected into a mold with the inverse of the micropattern to create the polymeric coating. Also, the polymeric material can be pulled through a mold using a vacuum pump system. In at least one embodiment, the polymeric coating can be created using soft lithography techniques. In one or more embodiments, etching techniques can be used to create the coating, wherein material is taken away from a layer of the coating material to create the micropattern of the polymeric coating 50. In yet another embodiment, a technique called hot embossing can be used, which involves stamping partially cured polymer into the desired shape of the polymeric coating and then curing it before it is applied to the stent. Stamping may or may not include the use of a solvent.

Figure 11:
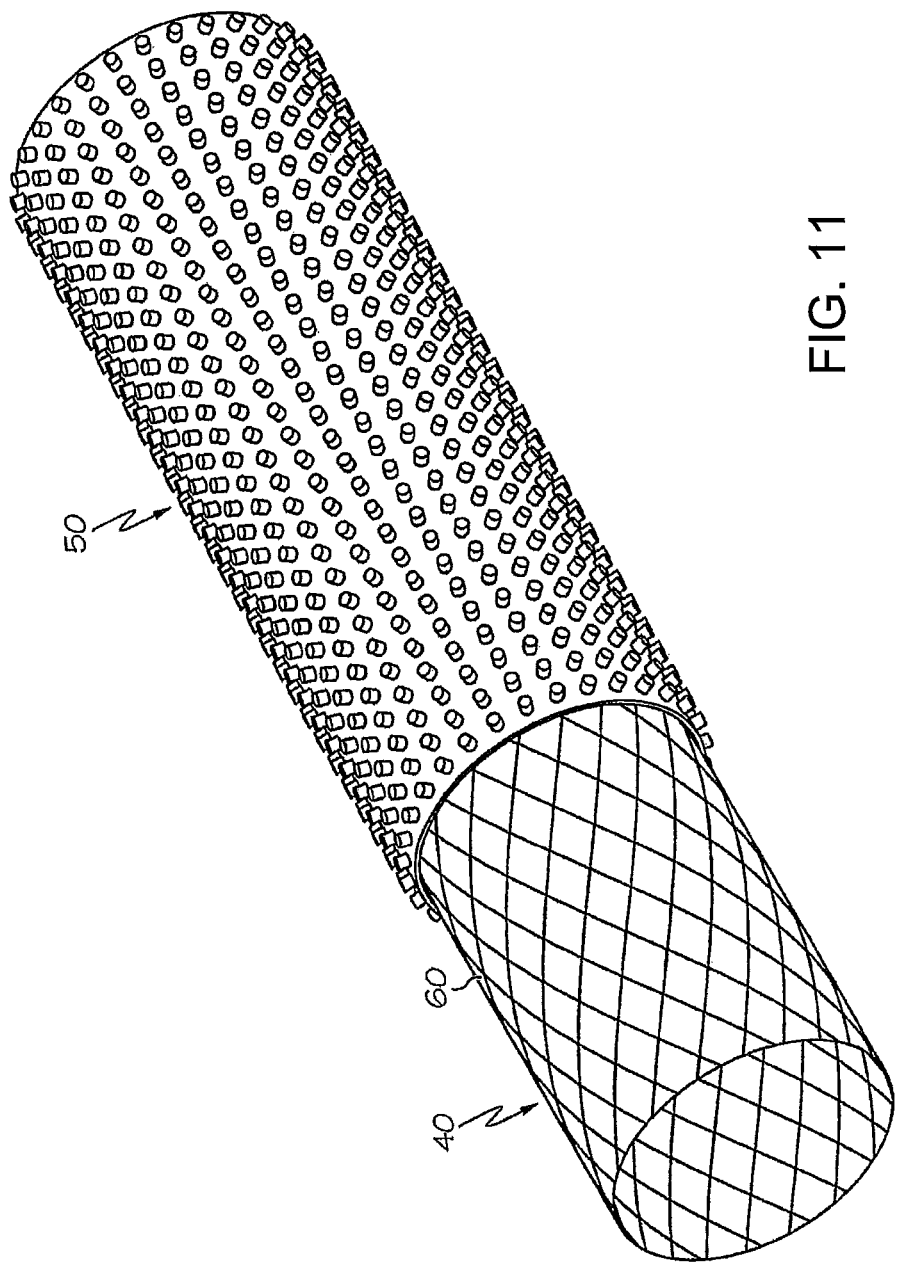
FIG. 11 is a view of the stent and polymeric coating during one method of manufacturing the endoprosthesis.
Figure 12:
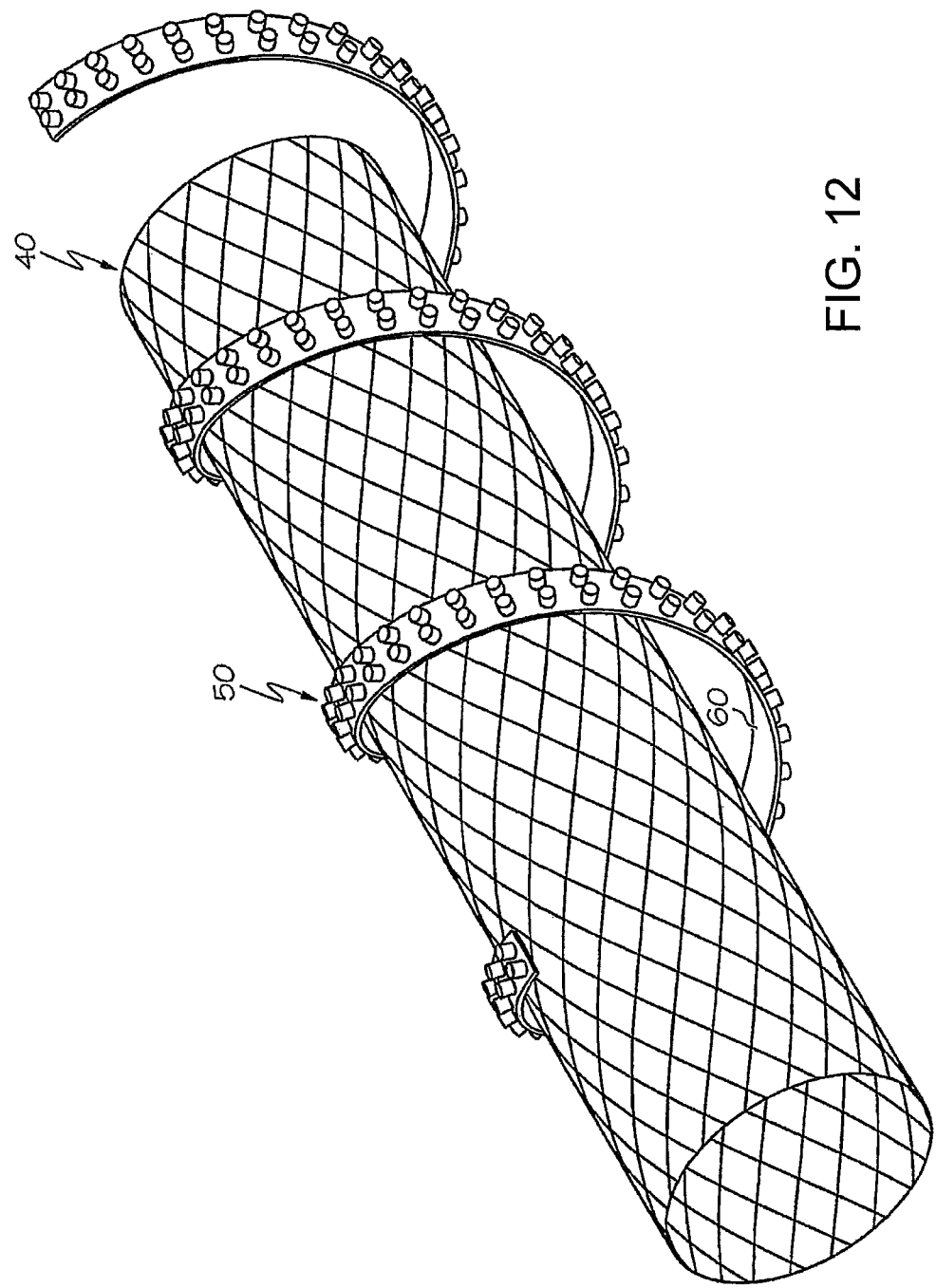
FIG. 12 is a view of the stent and polymeric coating during one method of manufacturing the endoprosthesis.
Figure 13:
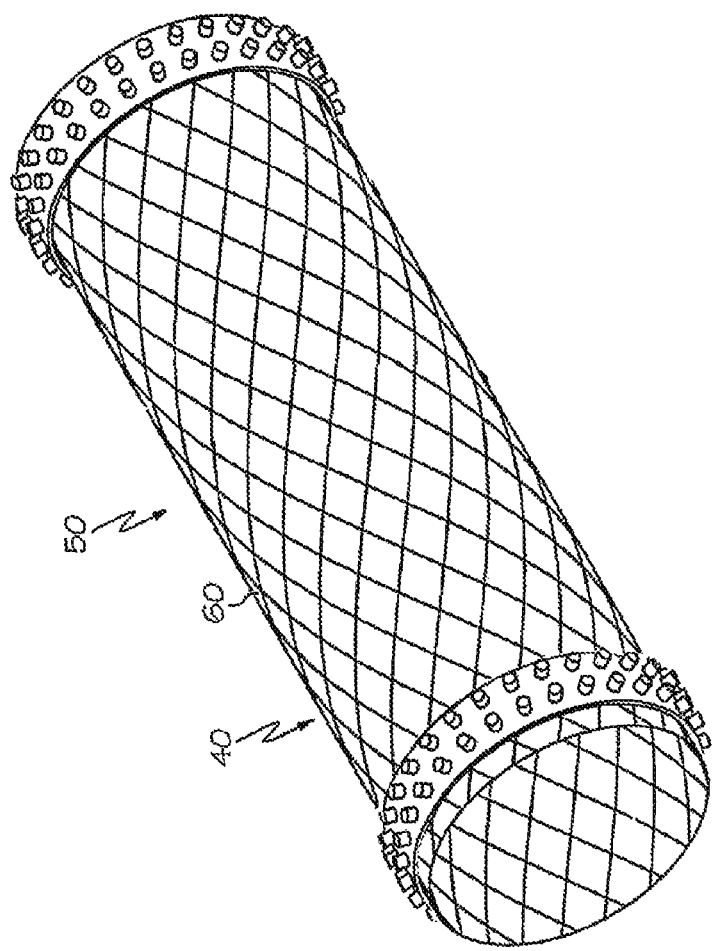
FIG. 13 shows an embodiment of the stent and polymeric coating of the present disclosure.
Figure 14:
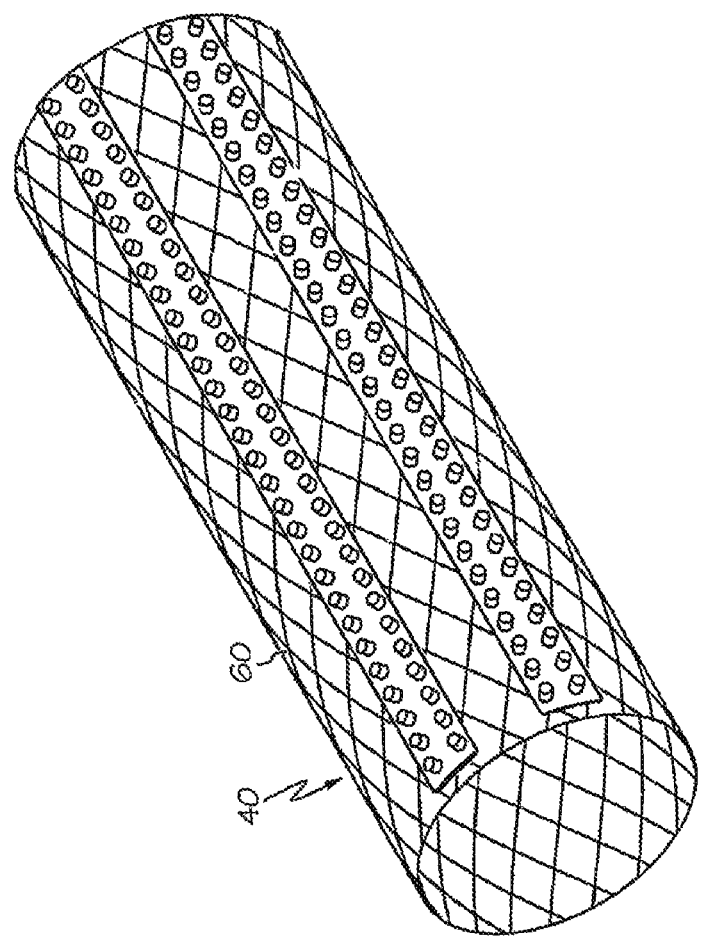
FIG. 14 shows an embodiment of the stent and polymeric coating of the present disclosure.

In at least one embodiment, as shown in FIG. 11, the coating 50 can be molded as a substantially tubular structure with a lumen defined by the base of the coating. An adhesive layer 60 can be applied to either the stent or to at least a portion of the inner surface of the base of the coating. In at least one embodiment, the adhesive layer 60 may substantially cover the entire inner surface of the base of the coating. The stent 40 can be inserted into the lumen of the coating 50. In at least one embodiment, heat and/or pressure may be applied to ensure proper adhesion of the coating 50 to the stent 40 via the adhesive layer 60. The adhesive layer may include silicone coatings, other suitable adhesives, or priming solutions that enable the coating to adhere to the metal stent (or stent coating thereon). In one or more embodiments, as shown in FIG. 12, rather than being molded as a tubular structure, the coating 50 can be molded as a strip attached to the outer surface 44 of the stent 40. In some embodiments, the strip can be applied as perimeter strips attached circumferentially about at least a portion of the circumferential perimeter of the stent, as shown in FIG. 13. In some embodiments, the strip can be a longitudinal strip attached to the stent in a longitudinal direction, as shown in FIG. 14. In some embodiments, the stent can be helically wrapped about the stent, as shown in FIG. 12. In some embodiments the coating may be applied as a single strip or as multiple strips. Where the coating is applied as multiple strips, directly adjacent strips may abut one another or may be spaced apart from one another. In at least one embodiment, the strips may be partial tubular structures that extend along the length of the stent but only cover a portion of the circumference of the stent. In some embodiments, a portion of stent 40 may be exposed. An adhesive layer 60 can be applied to either the stent or to at least a portion of the base of the coating. In at least one embodiment, heat and/or pressure may be applied to ensure proper adhesion of the coating 50 to the stent 40 via the adhesive layer 60. In at least one embodiment, discrete micropatterns of micropillars can be formed on and/or attached directly to either the stent 40 or the polymeric coating 50.

In one or more embodiments, the polymeric coating 50 can be formed by dip-coating the stent 40 in the coating material without needing an additional adhesive layer to connect the coating 50 to the stent 40. For instance, the stent 40 can be inserted into a mold, which includes a cavity and a tubular member. The cavity is defined by an inner wall of mold, which is an inverse of the desired micropattern. The stent 40 rests on the tubular member such that the inner surface of the stent is disposed about the tubular member. The mold with the stent 40 can be dipped into the coating material so that the coating material fills the mold and attaches to the stent 40. In some embodiments, temperature changes and/or pressure changes may be applied to the mold to cure the coating material. Once the coating material cures to form the polymer coating 50, the endoprosthesis 20 can be removed from the mold. Alternatively, the polymer coating 50 can be injection molded onto the stent using a similar mold. The coating material is injected into the mold rather than the mold being dipped into the coating material.

A description of some exemplary embodiments of the present disclosure is contained in the following numbered statements:

Statement 1. An endoprosthesis having an expanded state and an unexpanded state, the endoprosthesis comprising:
a stent, wherein the stent has an inner surface defining a lumen, an outer surface, a first end, a second end, and a thickness defined between the inner surface and the outer surface, wherein the stent has a plurality of openings extending through the thickness; and
a polymeric coating adhered to the outer surface of the stent, the polymeric coating comprising a base and a plurality of protrusions extending outwardly from the base, wherein the protrusions are arranged in a micropattern, wherein the base and the stent are coterminous, wherein the base covers the openings of the stent.

Statement 2. The endoprosthesis of statement 1, wherein when the endoprosthesis expands in a lumen defined by a vessel wall, the micropattern of protrusions apply a force that creates a desired interlock between the vessel wall and the endoprosthesis.

Statement 3. The endoprosthesis of statement 1 or statement 2, wherein the protrusions are micropillars selected from the group consisting of cylinders, rectangular prisms, and prisms with a polygonal base.

Statement 4. The endoprosthesis of any one of statements 1-3, wherein the protrusions of the micropattern are cylindrical micropillars, each cylindrical micropillar having a diameter and a height.

Statement 5. The endoprosthesis of any one of statements 1-4, wherein the diameter of the micropillar is between about 1 μm and 100 μm.

Statement 6. The endoprosthesis of any one of statements 1-5, wherein the diameter of the micropillar is between about 14 μm and 18 μm.

Statement 7. The endoprosthesis of any one of statements 1-6, wherein the height of the micropillar is between about 1 μm and 100 μm.

Statement 8. The endoprosthesis of any one of statements 1-7, wherein the height is between about 14 μm and 18 μm.

Statement 9. The endoprosthesis of any one of statements 4-8, wherein the diameter of the cylindrical micropillar is equal to the height of the cylindrical micropillar.

Statement 10. The endoprosthesis of any one of statements 4-9, wherein each cylindrical micropillar has a lateral surface, wherein the lateral surface of the cylindrical micropillar is separated from the lateral surfaces of an adjacent micropillar by a distance greater than the diameter of the cylindrical micropillar.

Statement 11. The endoprosthesis of any one of statements 1-10, wherein each protrusion of the micropattern has a first dimension and a second dimension, wherein the first dimension is between about 1 μm and 100 μm, wherein the second dimension is between about 1 μm and 100 μm, and wherein a ratio between the first dimension and the second dimension is between about 1 and 1.3.

Statement 12. The endoprosthesis of any one of statements 1-11, wherein the micropattern is a grid pattern.

Statement 13. The endoprosthesis of any one of statements 1-12, wherein the polymeric coating is a polymeric material selected from the group consisting of a hydrogel and a silicone.

Statement 14. The endoprosthesis of any one of statements 1-13, wherein the protrusions of the micropattern are uniform.

Statement 15. The endoprosthesis of any one of statements 1-13, wherein the micropattern includes protrusions of a first configuration and protrusions of at least a second configuration.

Statement 16. A method of manufacturing an endoprosthesis comprising:
forming a polymeric coating, wherein the polymeric coating comprises a base and a plurality of protrusions extending outwardly from the base in a micropattern;
providing a stent having an inner surface defining a lumen and an outer surface; and
adhering the base of the polymeric coating to the outer surface of the stent.

Statement 17. The method of statement 16, wherein the polymeric coating is formed using a mold having an inverse of the micropattern and injecting a polymeric material into the mold.

Statement 18. The method of statement 16 or statement 17, wherein an adhesive layer is applied to at least one of a surface of the base and the outer surface of the stent.

Statement 19. The method of any one of statements 16-18, wherein the polymeric coating is formed in a strip and helically wrapped about the outer surface of the stent.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to." Those familiar with the art may recognize other equivalents to the specific embodiments described herein which equivalents are also intended to be encompassed by the claims.

Further, the particular features presented in the dependent claims can be combined with each other in other manners within the scope of the present disclosure such that the present disclosure should be recognized as also specifically directed to other embodiments having any other possible combination of the features of the dependent claims.

This completes the description of the preferred and alternate embodiments of the present disclosure. Those skilled in the art may recognize other equivalents to the specific embodiment described herein which equivalents are intended to be encompassed by the claims attached hereto.

The invention claimed is:

1. An endoprosthesis having an expanded state and an unexpanded state, the endoprosthesis comprising:
a stent, wherein the stent has an inner surface defining a lumen, an outer surface, a first end, a second end, and a longitudinal axis extending therebetween, and a thickness defined between the inner surface and the outer surface, wherein the stent has a plurality of openings extending through the thickness;
an adhesive layer disposed on the outer surface of the stent; and
a plurality of spaced apart elongated polymeric strips disposed helically over and adhered to the adhesive layer, each elongated polymeric strip extending at least twice around a circumference of the stent, wherein a portion of the stent is exposed between longitudinally adjacent portions of a single polymeric strip, the plurality of spaced apart polymeric strips comprising a base having an inner surface and an outer surface including a plurality of protrusions extending outwardly from the base, wherein the protrusions are arranged in a micropattern, wherein the base covers the openings of the stent,
wherein each of the plurality of protrusions comprises a micropillar, each micropillar extending between a base portion at the base of the polymeric strip and a top surface at an end of the micropillar opposite the base portion.

2. The endoprosthesis of claim 1, wherein when the endoprosthesis assumes the expanded state in a lumen defined by a vessel wall, the micropattern of protrusions is adapted to apply a force that creates an interlock between the vessel wall and the endoprosthesis.

3. The endoprosthesis of claim 1, wherein each of the micropillars includes a columnar portion extending from the base portion toward the top surface, wherein at least a portion of the columnar portion is selected from the group consisting of cylinders, rectangular prisms, and prisms with a polygonal base.

4. The endoprosthesis of claim 3, wherein the micropillars each have a diameter at the base portion and a height extending between the base portion and the top surface.

5. The endoprosthesis of claim 4, wherein the diameter is between 1 μm and 100 μm.

6. The endoprosthesis of claim 5, wherein the diameter is between 14 μm and 18 μm.

7. The endoprosthesis of claim 4, wherein the height is between 1 μm and 100 μm.

8. The endoprosthesis of claim 7, wherein the height is between 14 μm and 18 μm.

9. The endoprosthesis of claim 4, wherein the geometric center of the top surface of the micropillar is separated from the geometric center of the top surface of an adjacent micropillar by a distance greater than the diameter of the micropillar.

10. The endoprosthesis of claim 1, wherein each protrusion of the micropattern has a height between the base portion and the top surface, and a diameter at the base portion, wherein the height is between 1 μm and 100 μm, wherein the diameter is between 1 μm and 100 μm, and wherein a ratio between height and the diameter is between 1 and 1.3.

11. The endoprosthesis of claim 1, wherein the polymeric member is made from a polymeric material selected from the group consisting of hydrogels and silicones.

12. The endoprosthesis of claim 1, wherein the protrusions of the micropattern are hollow.

13. The endoprosthesis of claim 1, wherein the micropattern includes protrusions of a first configuration and protrusions of at least a second configuration.

14. The endoprosthesis of claim 1, wherein first and second opposing walls of the micropillar extend between the base portion and the top surface at first and second angles, respectively, wherein the first and second angles are different from each other, and a geometric center of the base portion is offset laterally from a geometric center of the top surface.

15. The endoprosthesis of claim 1, wherein the micropillars have an outer surface, wherein at least some of the micropillars have recesses in their outer surface, the recesses distributed over substantially the entire outer surface.

16. An endoprosthesis having an expanded state and an unexpanded state, the endoprosthesis comprising:
a stent, wherein the stent has an inner surface defining a lumen, an outer surface, a first end, a second end, and a thickness defined between the inner surface and the outer surface, wherein the stent has a plurality of openings extending through the thickness; and a polymeric member adhered to the outer surface of the stent, the polymeric member comprising a base having an inner surface adhered to the stent and an outer surface including a plurality of elongate protrusions extending outwardly from the base, wherein the plurality of elongate protrusions are arranged in one or more different micropatterns, wherein each of the plurality of elongate protrusions extends from the base to a concave top surface.

17. The endoprosthesis of claim 16, wherein each elongate protrusion of the plurality of elongate protrusions has a height and a diameter at a base of the protrusion, wherein height is between 1 μm and 100 μm, wherein the diameter is between 1 μm and 100 μm, and wherein a ratio between the height and the diameter is between 1 and 1.3.

18. The endoprosthesis of claim 17, wherein a geometric center of each elongate protrusion of the plurality of elongate protrusions is spaced apart from a geometric center of adjacent elongate protrusions by a spacing between elongate protrusions, wherein a ratio of the spacing to the diameter is between 2.1 and 2.4.

19. An endoprosthesis having an expanded state and an unexpanded state, the endoprosthesis comprising:

a stent, wherein the stent has an inner surface defining a lumen, an outer surface, a first end, a second end, and a longitudinal axis extending therebetween, and a thickness defined between the inner surface and the outer surface, wherein the stent has a plurality of openings extending through the thickness; and a plurality of spaced apart elongated polymeric strips adhered to the stent with an adhesive layer, each of the plurality of elongated spaced apart polymeric strips extending helically around a circumference of the stent at least twice, each strip comprising a base having an inner surface facing the stent and an outer surface including a plurality of protrusions extending outwardly from the base, wherein the plurality of protrusions are arranged in one or more different micropatterns, wherein each of the plurality of protrusions extends between a base portion at the base of the polymeric strip and a top surface at an end of the protrusion opposite the base portion, wherein the top surface of each protrusion is concave, wherein the outer surface of the stent is exposed between longitudinally adjacent portions of a single polymeric strip and between the plurality of spaced apart polymeric strips.

20. The endoprosthesis of claim 19, wherein for at least some of the plurality of protrusions, first and second opposing walls of each protrusion extend between the base and a top surface of the protrusion at first and second angles, respectively, wherein the first and second angles are different from each other.

21. The endoprosthesis of claim 19, wherein a geometric center at the base of at least some of the plurality of protrusions is offset laterally from a geometric center of a top surface of the protrusion.

* * * * *